United States Patent [19]

DeWoskin

[11] 4,121,341
[45] Oct. 24, 1978

[54] ORTHODONTIC TRACTION APPARATUS

[75] Inventor: Irvin S. DeWoskin, St. Louis, Mo.

[73] Assignee: Orthoband Company, Inc., Barnhart, Mo.

[21] Appl. No.: 755,435

[22] Filed: Dec. 29, 1976

[51] Int. Cl.$^2$ ............................................. A61C 7/00
[52] U.S. Cl. ................................................. 32/14 D
[58] Field of Search ................................. 32/14 D, 20

[56] References Cited

U.S. PATENT DOCUMENTS

| 702,805 | 6/1902 | Lindas | 32/14 D |
|---|---|---|---|
| 2,968,097 | 1/1961 | DeWoskin | 32/14 D |
| 3,203,099 | 8/1965 | Interlandi | 32/14 D |
| 3,526,035 | 9/1970 | Armstrong | 32/14 D |
| 3,765,093 | 10/1973 | DeWoskin | 32/14 D |
| 3,772,789 | 11/1973 | DeWoskin | 32/14 D |

FOREIGN PATENT DOCUMENTS 803,016  9/1936  France ........................................ 32/20

*Primary Examiner*—Louis G. Mancene
*Assistant Examiner*—John J. Wilson
*Attorney, Agent, or Firm*—Koenig, Senniger, Powers and Leavitt

[57] ABSTRACT

Orthodontic traction apparatus for applying traction to the teeth of a patient comprising headgear to be worn by the patient including a pair of side members adapted to be positioned on opposite sides of the patient's head adjacent the ears, and a tensioning assembly on each side member for attachment to an instrumentality associated with the teeth for applying traction thereto. Each tensioning assembly comprises a rod mounted in a guide for sliding movement of the rod axially therein. The guide, in turn, is mounted on the respective side member for axial adjustment relative thereto and also for angular adjustment relative to the side member about an axis extending generally in side-to-side direction with respect to the patient's head. A spring biases the rod to slide axially in the guide to apply traction to the teeth.

12 Claims, 9 Drawing Figures

ORTHODONTIC TRACTION APPARATUS

BACKGROUND OF THE INVENTION

This invention relates to orthodontic appliances or instrumentalities and, more particularly, to extra-oral traction apparatus for applying traction to a patient's teeth via an orthodontic instrumentality.

Extra-oral devices are normally of the type in which the teeth are placed in traction by tensioning means connected to a neckband or headband, the traction being applied to the teeth via an orthodontic instrumentality on the teeth (e.g., a maxillary arch band or a mandibular arch band). The tensioning means may include two J-shaped rods, one one each side of the mouth extending back on the sides of the face and secured to the neckband or headband by a tensioning device. One such type of tensioning device is an elastic band arrangement such as is shown in U.S. Pat. Nos. 2,968,097 and 3,203,099. Use of an elastic band, i.e., a rubber band, has several disadvantages, however, one being that it is difficult precisely to establish the desired amount of traction with such an assembly. Moreover, such an assembly can be pulled beyond the point of no return, in which case it no longer exerts traction, and it might even snap or break.

These problems are alleviated by a second type of tensioning device in which traction is developed by compressing a member (e.g., a spring) rather than by applying tension to it. Reference may be made to U.S. Pat. Nos. 3,765,093 and 3,772,709 showing orthodontic traction devices of this general type. Generally, these latter prior art traction devices are adjustable by the orthodontist to apply a desired amount of traction force to the teeth. These devices have not, however, been readily adjustable for varying the angle at which such force is applied to the teeth. Moreover, these tensioning devices have not been readily adjustable from a high pull position especially suitable for applying traction to the upper teeth via a maxillary arch band or the like, to a low pull position especially suitable for applying traction to the lower teeth via a mandibular arch band.

SUMMARY OF THE INVENTION

Among the several objects of this invention may be noted the provision of orthodontic traction apparatus in which both the amount of traction force applied to the teeth and the angle at which such force is applied are readily adjustable; the provision of such apparatus which is adjustable from a high pull position for applying traction to the upper teeth via an orthodontic instrumentality on the upper teeth to a low pull position for applying traction to the lower teeth via an orthodontic instrumentality on the lower teeth; and the provision of such apparatus which is easy to use and of economical construction.

In general, apparatus of the invention comprises headgear to be worn by the patient including a pair of side members adapted to be positioned on opposite sides of the patient's head adjacent the patient's ears, and a tensioning assembly on each side member for attachment to an orthodontic instrumentality on the teeth for applying traction to the teeth. Each tensioning assembly comprises a generally thin, flat, narrow elongate arm having means at one end constituting its rearward end pivotally mounting it on a respective side member for pivoting relative to said side member about an axis extending generally in side-to-side direction with respect to the patient's head, said arm being adapted to extend forward from the side member on the patient's cheek toward the mouth. A fitting is provided at the outer end of said arm on the outside of the arm. An elongate tube is slidable axially in an opening in the fitting for axial adjustment relative to the fitting, the tube extending longitudinally with respect to said arm. A rod is slidable axially within the tube extending longitudinally of the tube and adapted for attachment at its forward end to said instrumentality. Means is provided for locking the tube in various positions of axial adjustment relative to the fitting. An elongate compression spring acts from the tube and extends rearwardly therefrom on the rod for biasing the rod to slide axially and rearwardly within the tube to apply traction to the teeth via said instrumentality. The amount of traction is adjustable by slidably adjusting the tube relative to said fitting and the arm being pivotable relative to the side member according to the angle at which traction is to be applied.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
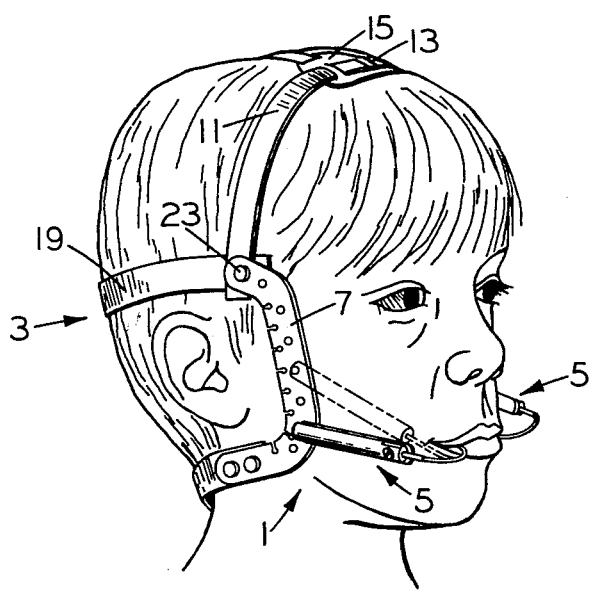
FIG. 1 is a view from the side illustrating orthodontic traction apparatus of this invention including the headgear worn by the patient and the tensioning assembly for applying traction to the teeth via an arch wire on the teeth.
Figure 2:
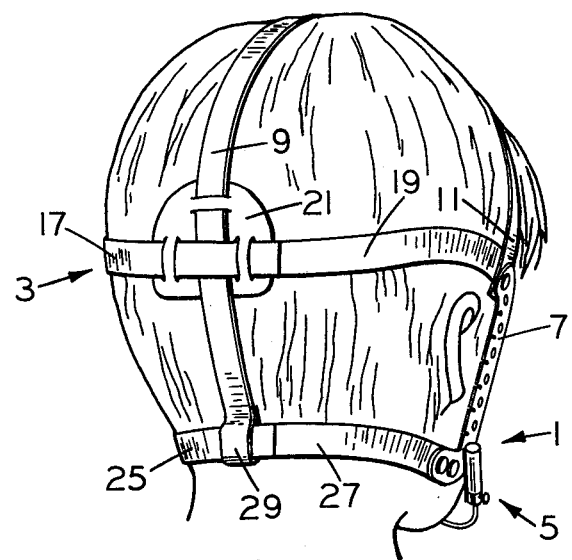
FIG. 2 is a view from the back of FIG. 1.

Referring to the drawings, first more particularly to FIGS. 1 and 2, orthodontic traction apparatus of this invention, indicated in its entirety at 1, is shown to include headgear generally indicated at 3 and a pair of tensioning assemblies each generally designated 5 secured to the headgear for attachment to an orthodontic instrumentality or instrumentalities (not shown) on the teeth in the patient's mouth for applying traction thereto. Such an instrumentality may be, for example, a maxillary arch band on the upper teeth or a mandibular arch band on the lower teeth. Each of the two tensioning assemblies is for a respective side of the patient's mouth.

The apparatus may be used to apply traction to both a maxillary arch band (in a generally upward and rearward direction) and also to a mandibular arch band (in a generally horizontal and rearward direction), and accordingly the headgear 3 is commonly referred to as a combination high pull-low pull headgear of the general type shown in my U.S. Pat. No. 2,968,097 (FIGS. 15 and 16). It comprises a pair of side plates, each generally indicated at 7, adapted to be worn flatwise on the respective side of the wearer's head in front of the respective ear, each side plate being of reverse C-shape with the generally vertical part of the plate in front of the respective wearer's ear and with the upper and lower portions of the plate extending generally rearwardly over the top and bottom portions of the ear, respectively. The headgear further includes an occipital strap 9 adapted to extend from the back of the neck of the patient upward to the top of the head. A right side overhead strap 11 extends from the upper portion of the C-plate 7 at the right side of the head to the top area of the head, and a left side overhead strap 13 extends upwardly from the upper portion of the left C-plate to the top of the head. A top adjustment piece 15 adjustably secures the upper ends of the occipital strap 9 and the right and left side overhead straps 11,13 at the top of the patient's head. Similarly, left and right back straps, designated 17,19, respectively, extend from the respective C-plates to a position at the back of the head where they are connected to the occipital strap 9 by a back adjustment piece 21. Overhead straps 11,13 and back straps 17,19 are secured to the upper portions of the C-plates by any suitable fasteners such as the rivets indicated at 23. Extending from the lower portions of the respective side plates 7 to a position at the back of the neck (cervix) are left and right cervical straps 25,27. The rearward ends of these straps 25,27 pass through a loop 29 at the lower end of the occipital strap 9 for adjustment relative thereto so as properly to fit the headgear 3 to the patient's head. The cervical straps are also secured to the side plates 7 by rivets although it will be understood that other fastening means may also be suitable. The straps of headgear 3 are made of any suitable flexible material. They may be plastic tapes, or may be made of cloth, leather or the like.

Figure 4:
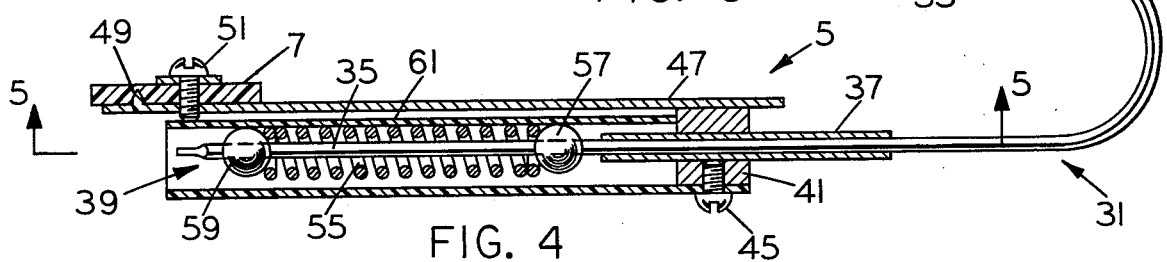
FIG. 4 is an enlarged section on line 4—4 of FIG. 3.
Figure 5:
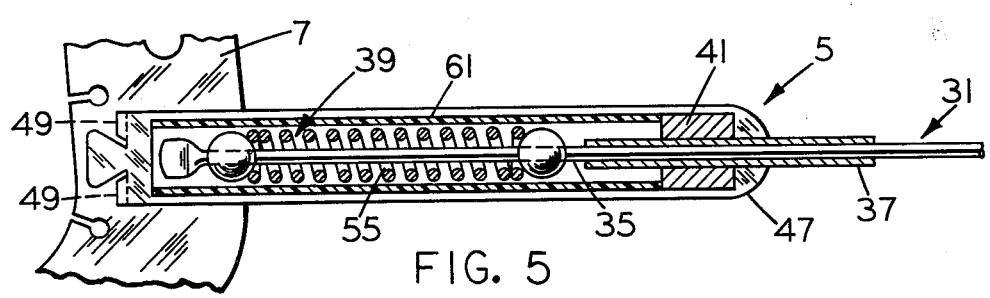
FIG. 5 is a section on line 5—5 of FIG. 4.

As shown in FIGS. 4 and 5, each tensioning assembly 5 of the instant invention comprises a J-shaped rod generally indicated at 31 having an eye 33 at its outer end (constituting its forward end) for attachment to an arch band or the like and a straight shank portion 35 axially slidable in guide means constituted by an elongate tube 37. The rod 31 is biased to slide axially in the tube 37 for applying traction to the teeth via the orthodontic instrumentality by spring means generally designated 39 acting from the rearward end of the tube and extending along the shank portion 35.

The elongate tube 37 is slidably mounted in a tubular fitting 41 for axial adjustment of the tube relative to the fitting thereby to allow the amount of traction force applied to the teeth via the orthodontic instrumentality to be accurately adjusted in accordance with the needs of the patient. With the rod 31 attached to an arch band, for example, adjustment of the tube 37 to the left (as viewed in FIGS. 4 and 5) with respect to the fitting 41 further compresses spring means 39 and causes greater traction to be applied to the teeth. Means such as a setscrew 45 is provided for locking the tube in its adjusted position. The tubular fitting 41 is mounted (as by brazing or soldering) on the outer (forward) end of a generally thin, flat, narrow elongate arm 47 which is, in turn, pivotally mounted at its rearward end on a respective side plate 7 for angular adjustment (pivoting) of the tensioning assembly 5 relative to the side plate about an axis extending generally in side-to-side direction with respect to the patient's head. The fitting is on the outside of the arm. Thus, the angle at which such traction force is applied may be selectively varied. In the embodiment of the invention shown in FIGS. 3–5, each arm 47 has a pair of prongs each designated 49 (see FIGS. 4 and 5) projecting inwardly from its rearward end for biting into the respective side plate 7 thereby to lock the arm to the plate in its adjusted angular position when a screw 51 is tightened to draw the arm toward the side member.

Figure 3:
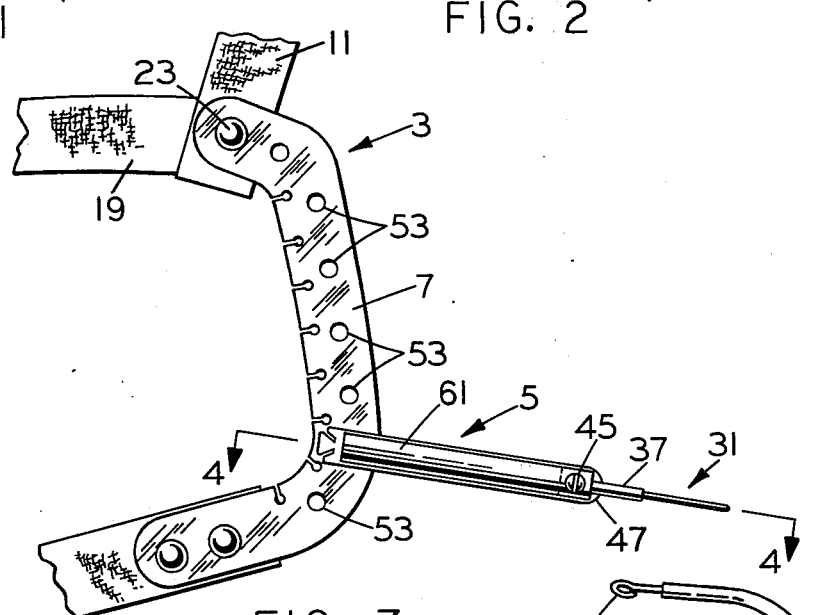
FIG. 3 is a view in side elevation of a portion of the headgear of this invention.

As shown in FIG. 3, each C-shaped side plate 7 has a series of holes, each designated 53, spaced lengthwise of the vertical part of the plate. The tensioning assembly 5 is adapted to be pivotally mounted at an elevation corresponding to any one of the holes by means of the screw 51 received in the hole and threaded into the rearward end of the arm 47, the screw acting as the pivot. Thus, the tensioning assembly may be selectively positioned at any one of a plurality of different elevations relative to the patient's mouth. This is especially desirable in that the tensioning assembly 5 should preferably be in a low pull position (shown in solid lines in FIG. 1) when applying traction to the lower teeth via the mandibular arch, and in a high pull position (shown in phantom) when applying traction to the upper teeth via the maxillary arch.

The spring means 39 includes an elongate coil compression spring 55 surrounding the shank portion 35 of the rod 31 between the tube 37 and the rearward end of the rod. As illustrated in the drawings, a first spring abutment 57 positioned between the elongate tube 37 and the forward end of the spring 55 and a second spring abutment 59 at the rearward end of the rod 31 are provided for engagement by the respective ends of the spring when the rod 31 is pulled forward to apply traction to the teeth. These spring abutments are preferably small balls having a diametrical passage therethrough in which the shank portion 35 has a slidable fit, although it should be understood that these abutments 57,59 could be fixedly secured to the rear end of the rod and the rearward end of the tube respectively. The rearward end of the shank portion 35 is pinched flat for engaging the rear spring abutment 59.

A sleeve 61 of clear plastic or the like is also provided for enclosing the rearward end of the rod 31 and the spring 55 thereon so that the spring is not likely to catch on the hair of the patient. The sleeve 61 is secured to the tubular fitting 41 by the setscrew 45 and extends rearwardly from the fitting for receiving the shank portion 35 of the rod and the spring 55 axially therein.

Figure 6:
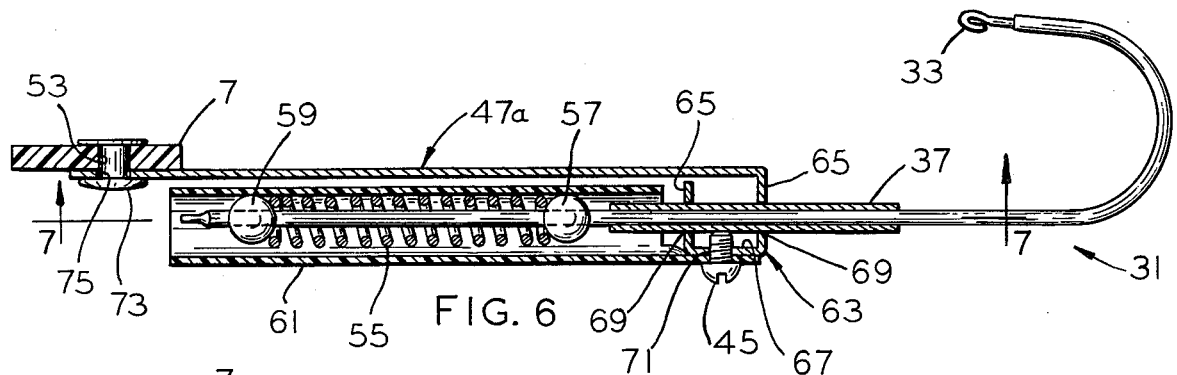
FIG. 6 is a view similar to FIG. 4 illustrating a second embodiment of the invention.
Figure 7:
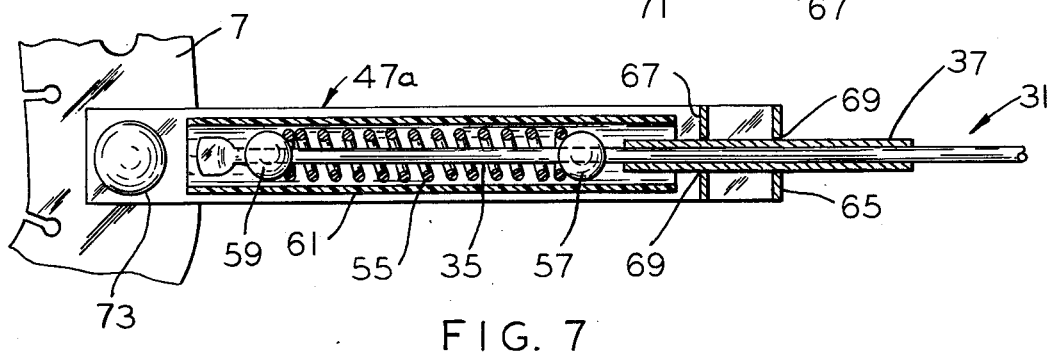
FIG. 7 is a section on line 7—7 of FIG. 6.

FIGS. 6 and 7 illustrate a second embodiment of the invention wherein the arm, which is designated 47a, is modified to provide the fitting for the slidable mounting of the tube 37 as an integral part of the arm, rather than as a separate piece mounted on the arm. For this purpose, the forward end portion of the arm 47a is bent to provide a U-shaped formation 63 at the outer end of the arm, the sides of the U being designated 65 and the base of the U being designated 67. The sides 65 and 67 have holes 69 slidably receiving the tube 37, which is locked in adjusted position by setscrew 45 threaded in a tapped hole at 71 in the base of the U. The arm 47a is pivotally mounted in a hole 53 in the plate 7 by means of a self-setting rivet 73 extending through a hole 75 in the arm, the arm being adapted freely to swivel on the rivet for angular adjustment. In this regard, arm 47a does not have the prongs 49 of the first embodiment, so that the arm is free to swivel, which may be preferred by orthodontists in many cases.

Figure 8:
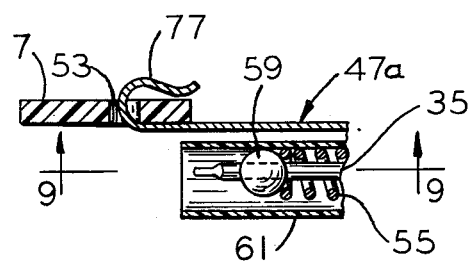
FIG. 8 is a fragmentary view similar to the left end portion of FIGS. 4 and 6 showing a third embodiment of the invention.
Figure 9:
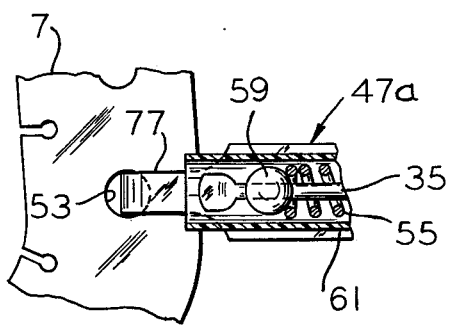
FIG. 9 is a section on line 9—9 of FIG. 8.

FIGS. 8 and 9 illustrate a third embodiment having arm 47a like FIGS. 6 and 7, but having the inner end of the arm formed as a hook 77 to hook into a hole 53 in the plate 7 (instead of using a rivet). Here again, the arm is free to swivel.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Orthodontic traction apparatus for applying traction to the teeth in a patient's mouth via an orthodontic instrumentality on the teeth comprising:

headgear including a pair of side members adapted to be worn on opposite sides of the patient's head adjacent the patient's ears;

each side member having a tensioning assembly associated therewith for attachment to said instrumentality for applying traction to the teeth;

each tensioning assembly comprising:

a generally thin, flat, narrow elongate arm having means at one end constituting its rearward end pivotally mounting it on a respective side member for pivoting relative to said side member about an axis extending generally in side-to-side direction with respect to the patient's head, said arm being adapted to extend forward from the side member on the patient's cheek toward the mouth;

a fitting on the other end of said arm on the outside of the arm;

an elongate tube slidable axially in an opening in the fitting for axial adjustment relative to the fitting, said tube extending longitudinally with respect to said arm;

a rod slidable axially within the tube extending longitudinally of the tube and adapted for attachment at its forward end to said instrumentality;

means for locking said tube in various positions of axial adjustment relative to the fitting; and an elongate compression spring acting from the tube and extending rearwardly therefrom on the rod for biasing the rod to slide axially and rearwardly within the tube to apply traction to the teeth via said instrumentality, the amount of said traction being adjustable by slidably adjusting the tube relative to said fitting and the arm being pivotable relative to the side member according to the angle at which traction is to be applied.

2. Apparatus as set forth in claim 1 wherein said arm has means at its rearward end for locking it in its adjusted angular position.

3. Apparatus as set forth in claim 2 wherein said locking means comprises means projecting from said arm for biting into said side member thereby to lock the arm to said side member.

4. Apparatus as set forth in claim 1 having a first spring abutment slidable on said rod between said guide means and the forward end of the spring for engagement therewith, and a second spring abutment at the rear end of the rod for engaging the rear end of the spring.

5. Apparatus as set forth in claim 1 further having an enclosure for said spring.

6. Apparatus as set forth in claim 5 wherein said enclosure comprises a sleeve secured to said arm receiving said rod and spring axially therein.

7. Apparatus as set forth in claim 1 wherein the fitting is formed by a bent portion of the arm.

8. Apparatus as set forth in claim 1 wherein each side member has a series of holes at different locations and the means pivotally mounting the arm thereon is received in one of said holes.

9. Apparatus as set forth in claim 8 wherein each said side member is a plate adapted to be worn flatwise on the respective side of the wearer's head in front of the respective ear, said plate being attached at its upper and lower ends to said headgear and said holes being spaced generally vertically of the plate.

10. Apparatus as set forth in claim 9 wherein said plate is of reverse C-shape and is adapted to be worn with the generally vertical part of the plate in front of the respective wearer's ear and with the upper and lower portions of the plate extending generally rearwardly over the top and bottom portions of the ear, respectively, said holes being spaced lengthwise of the vertical part of each plate.

11. Apparatus as set forth in claim 8 wherein said means pivotally mounting the arm on the side member comprises a rivet extending through a hole at the rearward end of the arm and through one of said holes in the side member.

12. Apparatus as set forth in claim 8 wherein said means pivotally mounting the arm on the side member comprises a hook at the rearward end of the arm received in one of said holes.

* * * * *